United States Patent
Matsui et al.

(10) Patent No.: US 6,960,454 B2
(45) Date of Patent: Nov. 1, 2005

(54) METHODS FOR MAKING AND USING A THERMOPHILIC ENZYME AS A β-GLYCOSIDASE

(75) Inventors: Ikuo Matsui, Ibaraki (JP); Kazuhiko Ishikawa, Ibaraki (JP); Hiroyasu Ishida, Ibaraki (JP); Yoshitsugu Kosugi, Ibaraki (JP)

(73) Assignee: Director-General of Agency of Industrial Science and Technology (JP)

( * ) Notice: Subject to any disclaimer, the term of this patent is extended or adjusted under 35 U.S.C. 154(b) by 0 days.

(21) Appl. No.: 09/369,735

(22) Filed: Aug. 6, 1999

(65) Prior Publication Data

US 2002/0102635 A1 Aug. 1, 2002

(30) Foreign Application Priority Data

Aug. 6, 1998 (JP) .......................................... 10-222866

(51) Int. Cl.$^7$ ..................... C12P 19/04; C12P 19/02; C12N 9/26; C12N 15/00; C07K 1/00

(52) U.S. Cl. ..................... 435/101; 435/105; 435/201; 435/325; 435/320.1; 435/252.3; 530/350

(58) Field of Search ................................. 435/201, 325, 435/252.3, 320.1, 105, 101, 6, 18; 530/350; 536/23.2

(56) References Cited

FOREIGN PATENT DOCUMENTS

WO    97/25417    * 7/1997

OTHER PUBLICATIONS

Ladrat et al., J. Mar. Biotechnol., 4, 192–199, Feb. 1996.*
Kawarabayasi et al., DNA Research, 5, 55–76, Apr. 1998.*
Sambrook et al., Molecular Cloning Laboratory Manual, second edition, Cold Spring Harbor Labratory Press, 1989.*

* cited by examiner

Primary Examiner—Maryam Monshipouri
(74) Attorney, Agent, or Firm—Fish & Richardson P.C.

(57) ABSTRACT

The invention relates to a thermophilic enzyme having β-glycosidase activity which comprises the amino acid sequence of SEQ ID NO: 2 in which one or a plurality of amino acid residues may be deleted, replaced or added.

12 Claims, 7 Drawing Sheets

FIG. 5

METHODS FOR MAKING AND USING A THERMOPHILIC ENZYME AS A β-GLYCOSIDASE

BACKGROUND OF THE INVENTION

The present invention relates to a thermophilic enzyme having β-glycosidase activity. More particularly, the present invention relates to a thermophilic enzyme having β-glycosidase activity derived from a hyperthermophilic bacterium belonging to the genus *Pyrococcus*.

β-Glycosidases are useful for hydrolysis of saccharides, DNA sequencing, conformational analysis of glycoproteins and glycolipids, and enzymatic synthesis of oligosaccharides and heterosaccharides with high optical purities. The catalytic reaction of β-glycosidases with substrates is specific with respect to the types of the monosaccharides constituting the substrates, and the optical isomerism and the position of the glycosidic linkage to be cleaved in the substrates. β-Glycosidases are also useful for the modification of sugar chains and the synthesis of oligosaccharides and polysaccharides retaining their optical stereoisomerism, as well as the synthesis of heterosaccharides (e.g., biosurfactants) due to their ability to transfer a glycoside group into a primary, secondary or tertiary alcohol. Hitherto, various types of β-glycosidases with different substrate-specificities have been found in bacteria and plants. However, since many of such β-glycosidases are derived from mesophilic organisms, they are poor in thermal resistance, and consequently are unsuitable for use in synthetic reactions under such extreme conditions that organic solvents are used simultaneously.

If a thermophilic β-glycosidase active in organic solvents is found, this can be used as an biocatalyst to develop a new procedure for synthesizing a heterosaccharide with high optical purity. In this procedure, the reverse hydrolytic reaction (i.e., synthetic reaction) is utilized which predominately occurs in the presence of an organic solvent. Under the circumstances, a novel β-glycosidase which is active under extreme conditions has been strongly demanded.

SUMMARY OF THE INVENTION

An object of the present invention is to provide a thermophilic enzyme with β-glycosidase activity.

For solving the above-mentioned problems, the present inventors focused on hyperthermophilic bacteria capable of growing within the temperature range from 90 to 100° C. As a result, they have found a gene that is assumed to encode a protein having β-glycosidase activity from its nucleotide sequence. The inventors have succeeded in the production of an enzyme from the gene by introducing the gene into *Escherichia coli* cells to transform the cells and then producing the enzyme from the transformants, which enzyme was confirmed to be stable at high temperatures (90° C. or higher) and to have β-glycosidase activity. This success leads the accomplishment of the invention.

That is, the present invention provides a thermophilic enzyme having β-glycosidase activity which comprises the amino acid sequence of SEQ ID NO: 2 in which one or a plurality of amino acid residues may be deleted, replaced or added. The number of the amino acid residue which may be deleted, replaced or added in the amino acid sequence of SEQ ID NO: 2 is not particularly limited as long as the β-glycosidase activity is retained, but preferably from 1 to 30, and more preferably from 1 to 18. It is preferable to delete, replace or add an amino acid residue or residues present in any of the regions of amino acid residues 78–86, 154–171 and 1–423. The enzyme preferably has an optimum temperature of 100° C. or higher.

The present invention also provides a DNA which is capable of hybridizing to the nucleotide sequence of SEQ ID NO: 1 or to the complement thereof under such conditions that the hybridization is carried out in 6×SSC and 50% formamide at 42° C. and the washing process is carried out in 6×SSC and 40% formamide at 25° C., and which encodes a thermophilic enzyme having β-glycosidase activity. These conditions are of low stringent. A moderate stringent conditions are such that the hybridization is carried out in 6×SSC and 40% formamide at 42° C. and the washing process is carried out in 1×SSC and 0% formamide at 55° C. A high stringent conditions are such that the hybridization is carried out in 6×SSC and 30% formamide at 42° C. and the washing process is carried out in 0.1×SSC and 0% formamide at 62° C. The DNA may encode a thermophilic enzyme which comprises the amino acid sequence of SEQ ID NO: 2 in which of one or a plurality of amino acid residues may be deleted, replaced or added and which has β-glycosidase activity.

The present invention further provides a recombinant vector containing the DNA therein, a host cell transformed with the recombinant vector, and a process for producing the enzyme comprising culturing a host cell transformed with an expression vector containing a DNA encoding the enzyme and then collecting the enzyme from the resultant culture. Using this process, the mass production of the enzyme becomes possible.

The present invention further provides a process for the hydrolysis of a β-glycoside having a long alkyl chain at the reducing end, with a thermophilic enzyme having β-glycosidase activity which comprises the amino acid sequence of SEQ ID NO: 2 in which one or a plurality of amino acid residues may be deleted, replaced or added. The long alkyl chain may be an alkyl group having carbon atoms of 8 or more. The hydrolysis may be carried out at a temperature of 85° C. or higher, and preferably 100° C. or higher.

This specification includes part or all of the contents as disclosed in the specification and/or drawings of Japanese Patent Application No. 10-222866, which is a priority document of the present application and incorporated herein by reference in its entirety.

The above and other objects, effects, features and advantages of the present invention will become more apparent from the following description of embodiments thereof taken in conjunction with the accompanying drawings.

BRIEF DESCRIPTION OF THE DRAWINGS

FIG. 5 shows aligned amino acid sequences (SEQ ID NOs: 2, 5–8) of five β-glycosidases from hyperthermophilic archaea. The abbreviations of the sources of the enzymes are: BGPh, βglycosidase from *P. horikoshii* (SEQ ID NO: 2); BMPh, a β-mannosidase gene homolog from *P. horikoshii* (8,9)(SEQ ID NO: 5); BGPf, β-glucosidase from *P. furiosus* (17)(SEQ ID NO: 6); BMPf, β-mannosidase from *P. furiosus* (17)(SEQ ID NO: 7); S β-gly, β-glycosidase from *Sulfolobus solfataricus* (18)(SEQ ID NO: 8); and the Consensus sequence (SEQ ID NO: 9). The conserved residues, identified automatically by the GeneWorks program, are shown in the open boxes. The reversed open triangles indicate the location of the nucleophile (E324) and the putative acid/base catalyst (E155 and H111) with R75 in the spatial proximity of the nucleophile of BGPh. The arrow shows the prominent deletion of more than 30 residues found in BGPh.

DESCRIPTION OF THE PREFERRED EMBODIMENT

Figure 1:
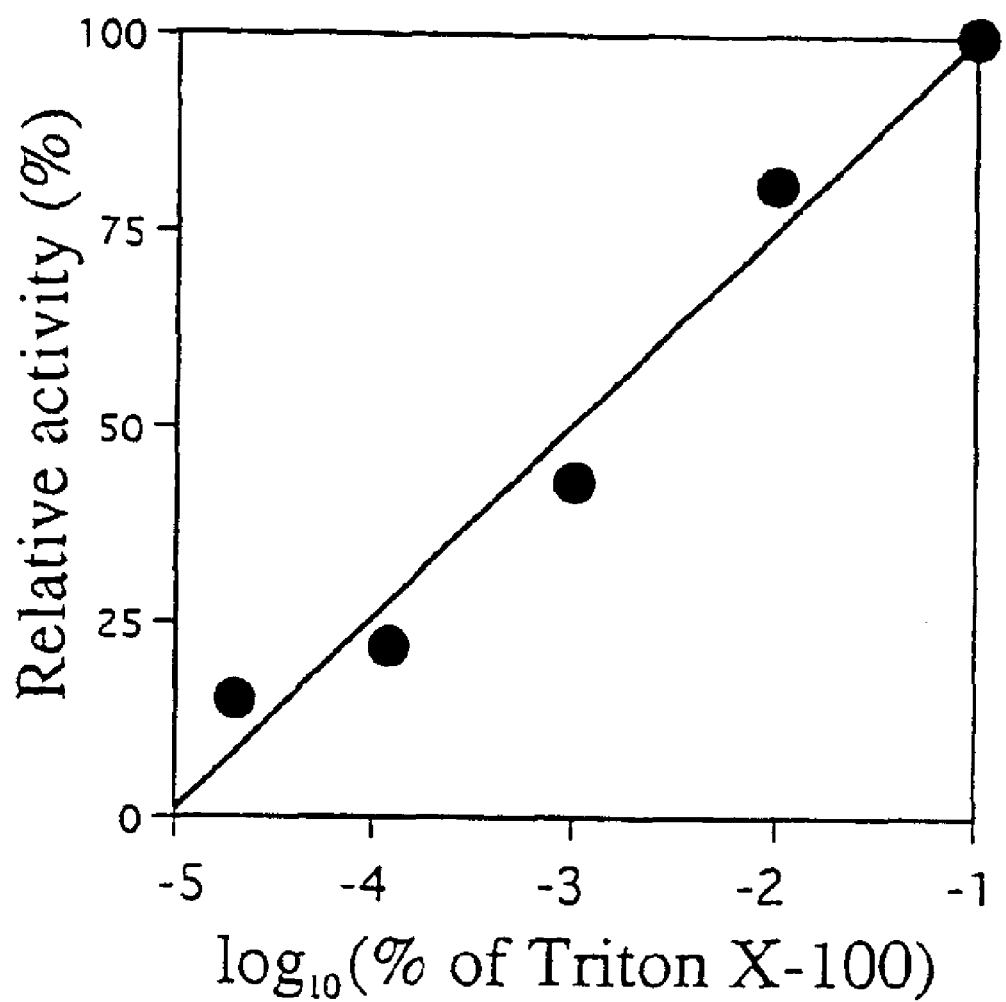
FIG. 1 shows the effect of the Triton X-100 concentration on the His-BGPh Activity. The standard of 100% was defined as the activity at 0.1% Triton X-100.

The present invention will be described specifically below.

The enzyme according to the present invention is a thermophilic enzyme having β-glycosidase activity which comprises the amino acid sequence of SEQ ID NO: 2 in which one or a plurality of amino acid residues may be deleted, replaced or added. The enzyme comprising an amino acid sequence of SEQ ID NO: 2 and having β-glycosidase activity is derived from a sulfur-metabolizable thermophilic archaeon *Pyrococcus horikoshii* (the accession number: JCM 9974). One example of the processes for producing the enzyme is described below.

First, cells of *Pyrococcus horikoshii* are cultured and then chromosomal DNA was prepared therefrom. The chromosomal DNA is digested with restriction enzyme(s) to give fragments, and a genomic DNA library is constructed using the fragments. Clones which cover the chromosome of *Pyrococcus horikoshii* are selected and aligned. The aligned clones are sequenced and a gene encoding a β-glycosidase is identified. The nucleotide sequence of the gene encoding β-glycosidase is depicted in SEQ ID NO: 1. The gene is amplified by the PCR method and then extracted. The extracted gene is inserted into an expression plasmid suitable for protein production (e.g., pET11a or pET15b). The resultant recombinant plasmid is introduced into cells of a host (e.g., *Escherichia coli*), from which the enzyme can be produced. The produced enzyme is isolated and purified by heating and then subjecting to column chromatography.

As a result, it is revealed that the purified enzyme is a protein having a molecular weight of about 45,000 Da and capable of hydrolyzing β-glycosides. When the enzyme is treated in 50 mM phosphate buffer (pH 6.0) containing 250 mM NaCl at 95° C. for 1 hour, its activity is retained at the level of 80% based on the initial level. The enzyme has an optimum pH of pH 6.0 and an optimum temperature of 100° C. or higher in terms of the enzymatic activity.

Variants of the enzyme, that is, thermophilic enzymes comprising deletion, replacement or addition of one or a plurality of amino acid residues in the amino acid sequence of SEQ ID NO: 2 and having β-glycosidase activity, may be prepared by any known techniques, such as site-specific mutagenesis and the PCR method.

The enzymes of the present invention can be used for hydrolysis of saccharides, DNA sequencing, conformational analysis of glycoproteins and glycolipids, synthesis of origosaccharides and heterosaccharides with high optical purities, and the like.

Deposit of Microorganism

A transformant designated "*E. coli* BL21 (DE3) pET15b/Gly2M" which is *E. coli* BL21 (DE3) transformed with an expression vector containing a β-glycosidase gene (pET15b/Gly2M) was deposited under the terms of the Budapest Treaty on Jul. 27, 1999 at the National Institute of Bioscience and Human-technology, Agency of Industrial Science and Technology, Japan (1–3, Higashi 1-chome, Tsukuba-shi, Ibaragi-ken, Japan) under Accession No. FERM BP-6800.

The following examples are given as more specific illustration of the invention. It should be understood, however, that the invention is not limited to the specific details set forth in the examples.

EXAMPLES

Abbreviations: BGPh, β-glycosidase from *P. horikoshii*; BMPh, β-mannosidase gene homolog from *P. horikoshii*; BGPf, β-glucosidase from *P. furiosus*; BMPf, β-mannosidase from *P. furiosus*; Sβ-gly, β-glycosidase from *Sulfolobus solfataricus*; Amp, ampicillin; IPTG, isopropyl-β-D-thiogalactopyranoside; His-BGPh, BGPh with His-tag; SDS-PAGE, sodium dodecyl sulfate-polyacrylamide gel electrophoresis; CBBR, Coomassie Brilliant Blue R; X-Glu, 5-bromo-4-chloro-3-indolyl-β-glucopyranoside; p-Nph-β-D-Glcp, p-nitrophenyl β-D-glucopyranoside; LA-β-D-Glcp, β-D-glucopyranosides with long alkyl chains.

Materials and Methods

Chemicals

The pET-11a vector and ultracompetent *E. coli* XL2-Blue MRF' cell were purchased from Stratagene. The pET-15b vector and *E. coli* strain BL21 (DE3) were obtained from Novagen. Vent DNA polymerase was purchased from New England Biolabs. Restriction enzymes were purchased from Promega and Toyobo (Osaka, Japan), and were used according to the manufacturers' recommendations. Ultrapure deoxynucleotide solution (dNTPs) was obtained from Pharmacia Biotech. Isopropyl-β-D-thiogalactopyranoside (IPTG) was from Takara Shuzo (Otsu, Shiga, Japan).

Cloning of Genes and Construction of Expression Vector

The genome of *P. horikoshii* was sequenced using the method of Kaneko et al. (10). Standard cloning techniques were used throughout. The expression vectors pET-11a and pET-15b were double-digested by the restriction enzymes Nde I and BamH I and the resulting 5.7 Kbp fragment was purified with a QIAquick Gel Extraction Kit (QIAGEN). The gene coding β-glycosidase (BGPh) was amplified by the PCR method using the following two primers: upper primer, TAAGAAGGAGATATACATATGCCGCT-GAAATTCCCGGAAATGTTTCTCTTTGGT ACC (SEQ ID NO: 3); lower primer, TTTACTGCAGAGAGGATC-CCTAATCCTAAAGTTGAAGTTCTGGTAG (SEQ ID NO: 4). The PCR product was cloned into expression vectors pET-11a and pET-15b using NdeI and BamHI sites.

The digested 1.3 Kbp fragment coding BGPh was purified and ligated to the insertion sites of the pET-11a and pET-15b vectors. Ultracompetent *E. coli* XL2-Blue MRF' cells were transformed with the recombinant molecule. Transformants were screened on 2×YT plates containing 50 mg/ml of ampicillin (Amp) incubated at 37° C. overnight. The transformant colonies were propagated in 5 ml 2×YT+Amp medium at 37° C. overnight and the vectors pET-11a/BGPh and pET-15b/BGPh were purified after centrifugation using a Mini Plasmid Kit (QIAGEN). The pET-11a/BGPh and pET-15b/BGPh were double-digested with NdeI and BamHI and the insert length was checked using agarose gel electrophoresis. The absence of additional mutations within the coding region of BGPh was verified by sequencing on an Applied Biosystems 373A DNA sequencer (Taq DyeDeoxy Terminator Cycle Sequencing Kit, PerkinElmer).

Overexpression and Purification of Recombinant Protein

The $E.\ coli$ strain BL21 (DE3) was transformed with the pET-11a/BGPh plasmid to express mature BGPh and pET-15b/BGPh plasmid to express His-tagged BGPh. The transformant colony was propagated as seed culture in 200 ml 2×YT+Amp medium at 37° C. overnight. An inoculate of 40 ml seed culture was inoculated to 2 l of 2×YT+Amp medium. The transformant was induced at OD600=1 with 1 mM IPTG for 4 h. The induced cells were collected by centrifugation and stored at −20° C.

The frozen cells (7 g) were thawed and mixed with 10 ml of 50 mM Tris-HCl buffer (pH 7.5) and 5.6 ml of 10% Triton X-100, resulting in a final concentration of 2.5%. The cell suspension was heated at 85° C. for 10 min, then centrifuged at 5000×g for 20 min. The supernatant was collected and stored at 4° C. The cell pellet was mixed with the same volume of the buffer and Triton X-100 and heated again. The heated sample was centrifuged at 25000×g for 20 min. The combined supernatant was mixed with 1 mg of bovine DNase 1 (Sigma) and incubated at 37° C. for 30 min. The supernatant was heated at 85° C. for 10 min, then centrifuged at 25000×g for 20 min to remove the inactivated DNase.

The solubilized recombinant BGPh with His-tag (His-BGPh) was subjected to affinity chromatography with Ni-conjugated Sepharose, using a stepwise elution from 5 mM to 1 M imidazole in 20 mM Tris-HCl (pH 8.0) with 0.5 M NaCl solution (His-bind Buffer Kit, Novagen) containing 0.1% Triton X-100. BGPh was eluted with 100 mM imidazole with 0.1% Triton X-100. The enzyme samples were analyzed by sodium dodecyl sulfate-polyacrylamide gel electrophoresis (SDS-PAGE) (11); a low molecular weight electrophoresis calibration kit, purchased from Pharmacia Biotech, was also run. For SDS-PAGE (PhastGel, 10–15%), the enzyme sample (5 ml) was mixed with SDS sample buffer (5 ml), boiled for 5 min, mixed with marker dye (1 ml) and applied to the gel in 1 or 4 ml aliquots. Following electrophoresis, protein was detected by Coomassie Brilliant Blue R (CBBR) staining according to the manufacturer's recommendation. The His-tagged protein was detected with QIAexpress Detection System (QIAGEN) after blotting onto a nitrocellulose membrane (Pharmacia Biotech).

Cellular Localization of the Activity

Localization of the BGPh activity in $E.\ coli$ transformant cells (BL21(DE3)/pET-11a/BGPh or BL21(DE3)/pET-15b/BGPh) was examined by fractionation of the cell components. The cell membrane was isolated as follows: 7 g of the induced cells, which were frozen at −20° C., were thawed and mixed with 10 ml of 50 mM Tris-HCl buffer (pH 7.5). The cell suspension (suspension I) was sonicated with a Sonifier 250 (Branson) for 4 min at an output control level of 4 and at 30% duty cycle. The sonicated sample was centrifuged at 9,000×g for 10 min to remove cell debris, then the supernatant (12 ml) was ultracentrifuged at 100,000×g for 1 h to separate the membrane fraction (1 ml) from the supernatant. The enzyme reactions were carried out at 90° C. for 15 min in a solution (200 ml) containing 1.2 mM 5-bromo-4-chloro-3-indolyl-β-glucopyranoside (X-Glu) and 5 ml of each fraction, as the enzyme source, in 50 mM phosphate buffer (pH 6) with 0.3 M NaCl. After the reaction, the solution was cooled in ice and diluted with 1 ml of water; the absorbance at 620 nm was immediately measured. As a control, the assay reactions were performed under the same conditions but without X-Glu to subtract the turbidity derived from each fractionated sample.

To analyze the solubilizing effect of Triton X-100, suspension I was also heated with and without 2.5% Triton X-100 at 85° C. for 10 min and the supernatant was obtained by centrifugation at 15,000×g for 10 min. The activity of the supernatants was measured using X-Glu as shown above.

Dependence of the BGPh Activity on Triton X-100

The enzyme reactions were carried out at 98° C. for 20 min in a solution (200 ml) containing 3 mM p-Nph-β-D-Glcp (a p-nitrophenyl saccharide) and 57.5 pM of the purified His-BGPh in 50 mM phosphate buffer (pH 6) with Triton X-100 and 0.1 M NaCl. The concentration of Triton X-100 in the reaction solution was varied from 0.1% to 0.00002%. The reaction was terminated by the addition of 1 M Na2CO3 (1 ml), then centrifuged at 15,000×g for 10 min. The concentration of the p-Nph group in the supernatant was quantified by measuring the absorbance at 400 nm.

Measurement of the Kinetic Parameters

The enzyme reactions were carried out at 90° C. in a solution (200 ml) containing the substrate and the purified His-BGPh in 50 mM phosphate buffer (pH 6) with 0.1% Triton X-100 and 0.3 M NaCl. For the hydrolysis of p-nitrophenyl (p-Nph) β-D-saccharides, the reaction was terminated by the addition of 1 M Na2CO3 (1 ml), then centrifuged at 15,000×g for 10 min. The concentration of the p-Nph group in the supernatant was quantified by measuring the absorbance at 400 nm. For the hydrolysis of β-D-glucoside, the released glucose was analyzed with a Glucose C-II Test kit (Wako Pure Chemicals, Japan). Initial velocities were obtained directly from the initial slopes of the time course plots. The Km and kcat values were calculated using the Michaelis-Menten equation and the least squares method (12). The subsite affinity for a long alkyl chain was determined using the method reported previously (13–15) on the basis of the subsite theory (16).

Optimum Temperature and Optimum pH

The optimum temperature was measured as follows: the assay mixture (200 ml), which contained 3 mM p-nitrophenyl β-D-glucopyranoside (p-Nph-β-D-Glcp) in 150 mM citrate buffer (pH 5.0) and 1 ml of suspension I (BL21(DE3)/pET-11a/BGPh), was heated at 85° C. for 10 min. The enzyme reactions were carried out in duplicate at temperatures ranging from 50° C. to 100° C. for 30 min. Optical density measurements at A405 were performed as described for the enzyme assays.

To determine the optimum pH, the assay mixture (200 ml), which contained 1 ml of heated suspension I (BL21 (DE3)/pET-11a/BGPh or BL21(DE3)/pET-15b/BGPh) and p-Nph-β-D-Glcp (3 mM) in 139 mM buffer systems, was heated at 90° C. for 30 min. The pH of the reaction mixtures ranged from 3.9 to 5.5 in sodium acetate buffer and from 5.5 to 7.99 in phosphate buffer. Optical density measurements at A405 were performed as described for the enzyme assays.

Thermostability

The His-BGPh solutions (29 nM) in 50 mM phosphate buffer (pH 6.0) containing 100 mM NaCl and 0.1% Triton X-100 were heated in sealed Eppendorf tubes at 90° C. in various increments up to 24 h. The heated enzymes were assayed in duplicate in phosphate buffer (pH 6.0) at 90° C. for 20 min as described for the determination of optimum temperature.

Sequence Alignment, Phylogenetic Tree, and Hydropacy Profile

Sequence alignment of β- glycosidases was performed using the GeneWorks program (IntelliGenetics, Inc.) based on a PAM-250 scoring matrix. The enzymes of interest were:

β-glycosidase (BGPh) studied in this paper and β-mannosidase (BMPh) from *P. horikoshii* (8, 9), β-glucosidase (BGPf) and β-mannosidase (BMPf) from *P. furiosus* (17), and β-glycosidase (Sβ-gly) from *Sulfolobus solfataricus* (18). Phylogenetic trees for the same sequences were constructed using the GeneWorks program based on the unweighted pair group method with an arithmetic mean (19). Each hydropacy profile was analyzed with DNASIS-Mac v2.0 software based on the Kyte and Doolittle method (20).

Results and Discussion

Localization of the Activity in *E. coli* Membrane

The intracellular localization of His-BGPhwas examined (Table I).

X-100 at 85° C. for 15 min. The native-type BGPh was also solubilized under the same condition as His-BGPh (data not shown); however, the denaturation with 8 M urea and the renaturation by direct dilution with buffer had no effect on the solubilization of the activity (data not shown). These facts strongly indicate that BGPh is a thermostable membrane protein solubilized by Triton X-100.

His-BGPh was purified by one-step affinity chromatography using Ni-conjugated Sepharose. Since the recovery of the active enzyme was decreased to a few percent by the elimination of Triton X-100 from the chromatographic washing and elution buffers, the presence of Triton X-100 in the buffer system was essential for the stabilization of BGPh.

As shown in FIG. 1, the activity of BGPh was dependent on the concentration of Triton X-100. At 0.00002% Triton X-100, the activity decreased to 10% of that with 0.1%

TABLE I

Cellular localization of the activity. The transformant *E. coli* BL21(DE3)/pET15b/BGPh cells were used for this experiment. The enzyme reaction were performed at 90° C. and pH 6 for 15 min using X-Glu as substrate, and then $A_{620}$ was measured as shown in "MATERIALS AND METHODS".

| | Activity after each treatment ($A_{620}$) | | | | |
|---|---|---|---|---|---|
| Cell fractions | Sonication | Non-heated | Heated | Non-heated with 2.5% Triton X-100 | Heated with 2.5% Triton X-100 |
| Suspension I | 0.585 | 0.585 | 0.567 | 0.485 | 0.428 |
| Supernatant at 9,000 xg | 0.112 | ND | ND | ND | ND |
| Supernatant at 15,000 xg | ND | 0.008 | 0.005 | 0.107 | 0.255 |
| Supernatant at 100,000 xg | 0.010 | ND | ND | ND | ND |
| Fraction precipitated at 100,000 xg | 0.478 | ND | ND | ND | ND |

ND; not determined.

Figure 2:
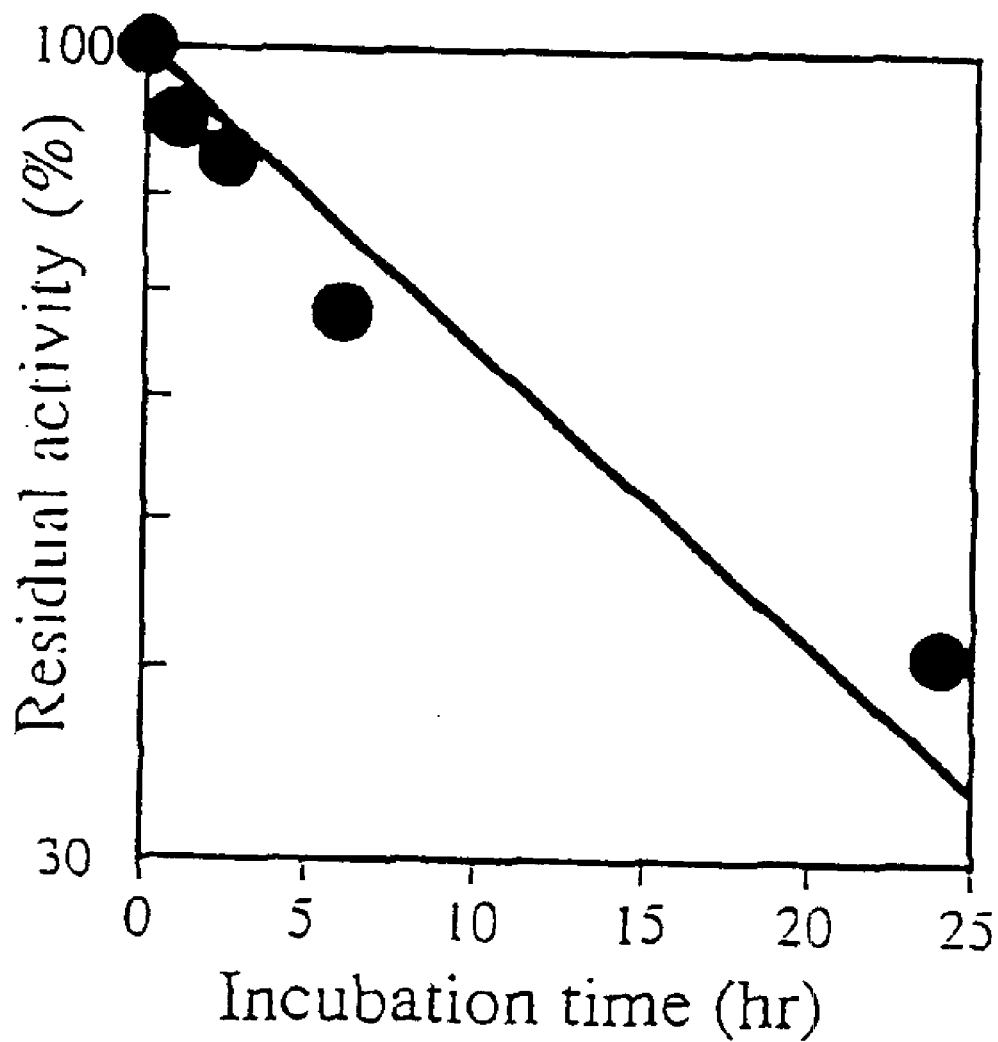
FIG. 2 shows thermostability of His-BGPh at 90° C. Triton X-100 at 0.1% was present in the reaction mixtures. The standard of 100% was defined as the activity without heating.

The induced cells were disrupted by sonication and centrifuged to separate the cell components. The membrane fraction was precipitated by ultracentrifugation at 100,000×g from the supernatant recovered by centrifugation at 9,000×g. The activity was present in the membrane fraction whereas no activity was detected in the soluble fraction after the ultracentrifugation. His-BGPhwas solubilized from the cell suspension (suspension I) by heating with a detergent, Triton X-100; the enzyme was not solubilized by heating without Triton X-100. The solubilizing efficiency with Triton X-100 was elevated by heating up to 85° C., whereas only 22% of the activity was extracted at room temperature. The best condition for the solubilization was 2.5% Triton Triton X-100. Furthermore, BGPh was stabilized in the presence of 0.1% Triton X-100: the half-life of the activity was 15 h at 90° C. and pH 6.0 (FIG. 2). These facts also suggest that BGPh is the membrane protein.

The Substrate Specificity of BGPh

Figure 3:
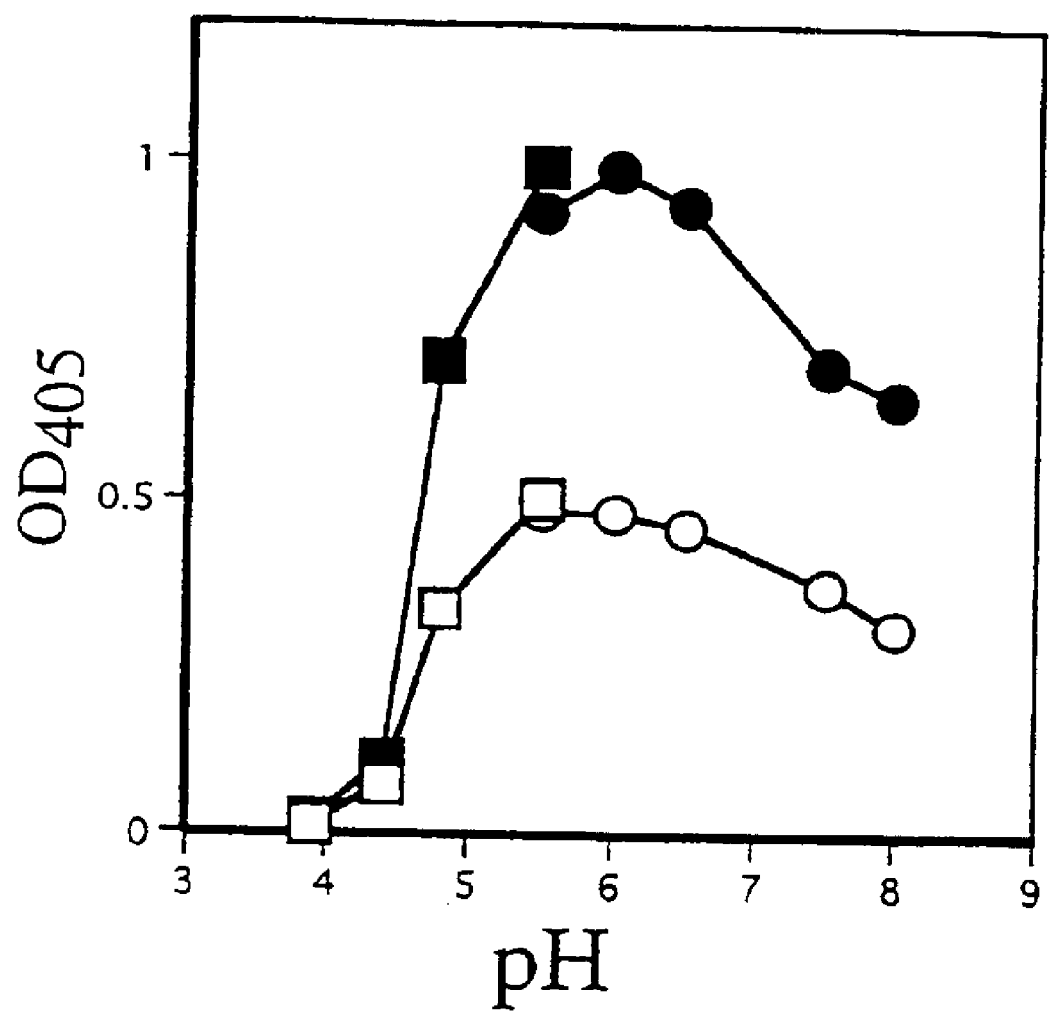
FIG. 3 shows optimum pH of the activity for His-BGPh. The OD405 indicates the amount of released p-Nph group in acetate buffer (square) and phosphate buffer (circle). The closed symbols correspond to the activity of BGPh and open symbols correspond to the activity of His-BGPh. For these measurements, equal amounts of BGPh and His-BGPh were used because the heated suspension I (BL21(DE3)/pET-11a/BGPh or BL21(DE3)/pET-15b/BGPh) was estimated to contain the same amount of each induced protein by quantification using SDS-PAGE analysis.
Figure 4:
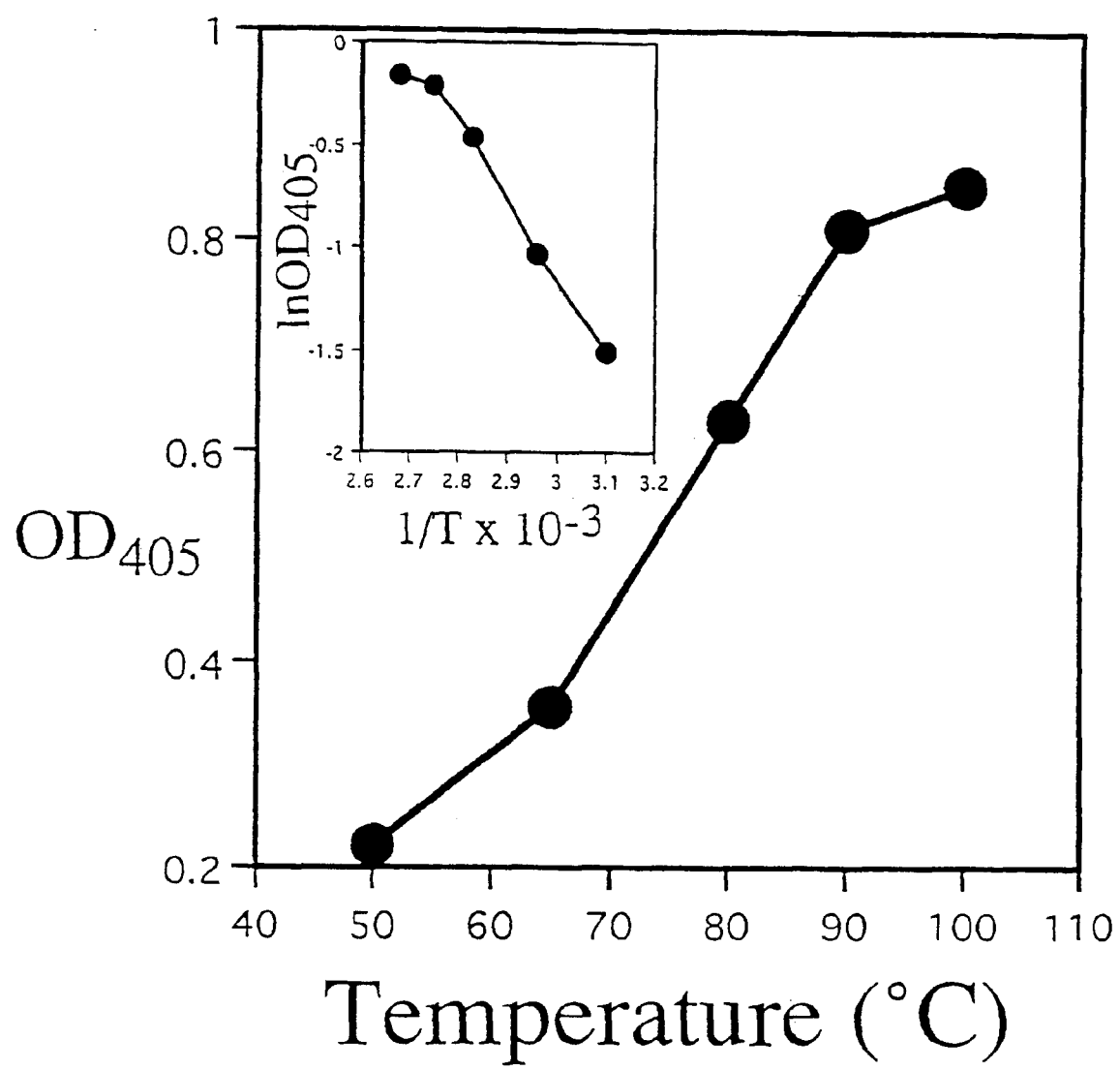
FIG. 4 shows temperature dependency of BGPh. Optimum temperature was determined by the plots of enzymatic activity (OD405 nm change) against reaction temperature. An Arrhenius plot of the data is given in the inset.

For BGPh both with or without His-tag, the optimum pH was 6.0 (FIG. 3) and the optimum temperature was over 100° C. (FIG. 4). The substrate specificity of His-BGPh was examined using p-Nph-β-D-saccharides and β-D-glucosides as substrates. The specificity is summarized in Table II in comparison with that of Sβ-gly (7, 21).

TABLE II

Comparison of the kinetic parameters between his-tagged BGPh from *P. horikoshii* and Sβ-gly from *S. solfataricus* strain MT-4 against p-Nph-β-D-saccharides and β-D-glucosides.

| | His-BGPh (90° C. and pH 6.0) | | | Sβ-gly[a] (75° C. and pH 6.5) | | |
|---|---|---|---|---|---|---|
| Substrates | $k_{cat}$ (sec$^{-1}$) | $K_m$ (mM) | $k_{cat}/K_m$ (mM$^{-1}$sec$^{-1}$) | $k_{cat}$ (sec$^{-1}$) | $K_m$ (mM) | $k_{cat}/K_m$ (mM$^{-1}$sec$^{-1}$) |
| Laminaribiose | 184 | 138.23 | 1.33 | 908 | 1.0 | 908.0 |
| Cellobiose | 194 | 1698.18 | 0.11 | 1333 | 30.0 | 44.4 |
| Cellotriose | ND[b] | ND | ND | 197 | 3.0 | 66 |
| Cellotetraose | ND | ND | ND | 584 | 1.7 | 343 |
| β-Gentiobiose | ND | ND | ND | 1360 | 100 | 14 |
| p-Nph-β-D-Glcp | 79 | 0.35 | 225.67 | 542 | 0.5 | 1084.0 |
| p-Nph-β-D-Galp | 123 | 1.30 | 94.34 | 1020 | 4.7 | 217.0 |
| p-Nph-β-D-Xylp | 3 | 0.10 | 31.83 | 284 | 4.0 | 71.0 |
| p-Nph-β-D-Manp | 2 | 0.14 | 14.60 | NH[c] | NH | NH |
| Salicin | 44 | 1.96 | 22.20 | 880 | 5.0 | 175.9 |
| Methyl-β-D-Glcp (Alkyl: $C_1$) | 35 | 40.74 | 0.85 | —[d] | — | — |
| n-Amyl-β-D-Glcp (Alkyl: $C_5$) | 31 | 2.02 | 15.11 | 256 | 1.1 | 232 |

TABLE II-continued

Comparison of the kinetic parameters between his-tagged BGPh from *P. horikoshii* and Sβ-gly from *S. solfataricus* strain MT-4 against p-Nph-β-D-saccharides and β-D-glucosides.

| | His-BGPh (90° C. and pH 6.0) | | | Sβ-gly[a] (75° C. and pH 6.5) | | |
|---|---|---|---|---|---|---|
| Substrates | $k_{cat}$ (sec$^{-1}$) | $K_m$ (mM) | $k_{cat}/K_m$ (mM$^{-1}$sec$^{-1}$) | $k_{cat}$ (sec$^{-1}$) | $K_m$ (mM) | $k_{cat}/K_m$ (mM$^{-1}$sec$^{-1}$) |
| n-Hexyl-β-D-Glcp (Alkyl: $C_6$) | 33 | 0.54 | 60.28 | 263 | 1.0 | 263 |
| n-Octyl-β-D-Glcp (Alkyl: $C_8$) | 34 | 0.20 | 170.70 | 313 | 0.7 | 434 |
| n-Nonyl-β-D-Glcp (Alkyl: $C_9$) | 39 | 0.08 | 471.57 | — | — | — |
| n-Decyl-β-D-Glcp (Alkyl: $C_{10}$) | 37 | 0.08 | 469.62 | — | — | — |
| n-Undecyl-β-D-Glcp (Alkyl: $C_{11}$) | 43 | 0.05 | 944.37 | — | — | — |
| n-Dodecyl-β-D-Glcp (Alkyl: $C_{12}$) | 36 | 0.03 | 1152.90 | — | — | — |

[a]Cited from references (7, 21).
[b]ND; The parameters were not determined because of too high $K_m$ values.
[c]NH; The substrate was not hydrolyzed by Sβ-gly.
[d]—; The parameters were not reported in the references.

His-BGPh hydrolyzed aryl glycosides efficiently, showing kcat/Km values decreasing in the order p-Nph-β-D-Glcp>p-Nph-β-D-Galp>p-Nph-β-D-Xylp>p-Nph-β-D-Manp. Beta-linked glucose dimers tested were poorly hydrolyzed; the order of preference was β 1–3>β 1–4>β1–6. The kcat values of BGPh without His-tag for these β-linked glucose dimers approached 400 sec$^{-1}$, which is comparable with those of Sβ-gly (Table II). His-BGPh probably had approximately 50% of the activity of BGPh due to interference by the His-tag located at the N-terminus, (FIG. 3). Surprisingly, the best substrates for His-BGPh were β-D-glucosides with long alkyl chains (LA-β-D-Glcp) The Km values decreased according to the elongation of the alkyl chain from $C_1$ to $C_{12}$, although the kcat value was constant (approximately 35 sec$^{-1}$) for each alkyl-β-D-Glcp. The kcat values of native type BGPh for LA-β-D-Glcp approached 70 sec$^{-1}$, calculated on the basis of the value of His-BGPh, estimating a 50% decrease in the activity from the inhibitory effect of the His-tag. The value was also appreciable, around 30% of that of Sβ-gly (Table II). The Km value of His-BGPh for the hydrolysis of n-Dodecyl-β-D-Glcp (alkyl chain: $C_{12}$) was extremely low, 30 mM at 90° C. and pH 6.0. Of the substrates examined thus far, the best substrate was n-Dodecyl-β-D-Glcp as shown in Table II. The kcat/Km value of His-BGPh against n-Dodecyl-β-D-Glcp was 5 times higher than that of p-Nph-β-D-Glcp and 870 times higher than that of laminaribiose. Even the value for n-Octyl-β-D-Glcp was 0.76 times higher than that of p-Nph-β-D-Glcp and 128 times higher than that of laminaribiose. The kcat/Km value of Sβ-gly against n-Octyl-β-D-Glcp, with the longest alkyl chain so far examined (21), was 0.4-fold higher than that for p-Nph-β-D-Glcp and 0.48-fold higher than that for laminaribiose. Laminaribiose and cellobiose were not good substrates for the hydrolysis of His-BGPh because of their Km values higher than 100 mM. His-BGPh also hydrolyzed cellotriose and cellotetraose with low efficiency: the kinetic parameters were not determined because of the extremely high Km value, whereas Sβ-gly was able to hydrolyze these oligosaccharides with high efficiency: the kcat/Km values descended in the order; cellotetraose>cellotriose>cellobiose. Thus, the substrate specificity of His-BGPh is different from those of the other β-glycosidases, including Sβ-gly (7, 17, 21–23). BGPh has a novel substrate specificity with high efficiency to hydrolyze LA-β-D-Glcp and low efficiency to hydrolyze any β-linked glucose dimer which is more hydrophilic than aryl- or alkyl-β-D-Glcp. The subsite affinity ($A_{(C11)}$) to bind a long alkyl chain $_{(C11)}$ was calculated according to the following equation; $A_{(C11)} = RT\, ((k_{cat}/K_m)_{for\ n\text{-}Dodecyl\text{-}\beta\text{-}D\text{-}Glcp}/(k_{cat}/K_m)_{for\ Methyl\text{-}\beta\text{-}D\text{-}Glcp})$. The affinity was determined to be 4.26 kcal/mol. The value was reasonable when compared with the highest affinity (4.23 kcal/mol) known, that of the recognition of one glucose unit in the subsite structure of Saccharomycopsis amylase (13, 14). These facts indicate that the hydrophobicity of the aglycon part of the substrates is strongly recognized by the BGPh molecule and the hydrophobic substrates, including aryl- and LA-β-D-Glcp, are hydrolyzed effectively with low Km values due to hydrophobic interaction between the aglycon moiety and the BGPh molecule. Thus, BGPh might be useful to synthesize novel β-glycosides, including new biosurfactants, using its transglycosylation activity because of its stability in organic solvents (data not shown).

Figure 5:
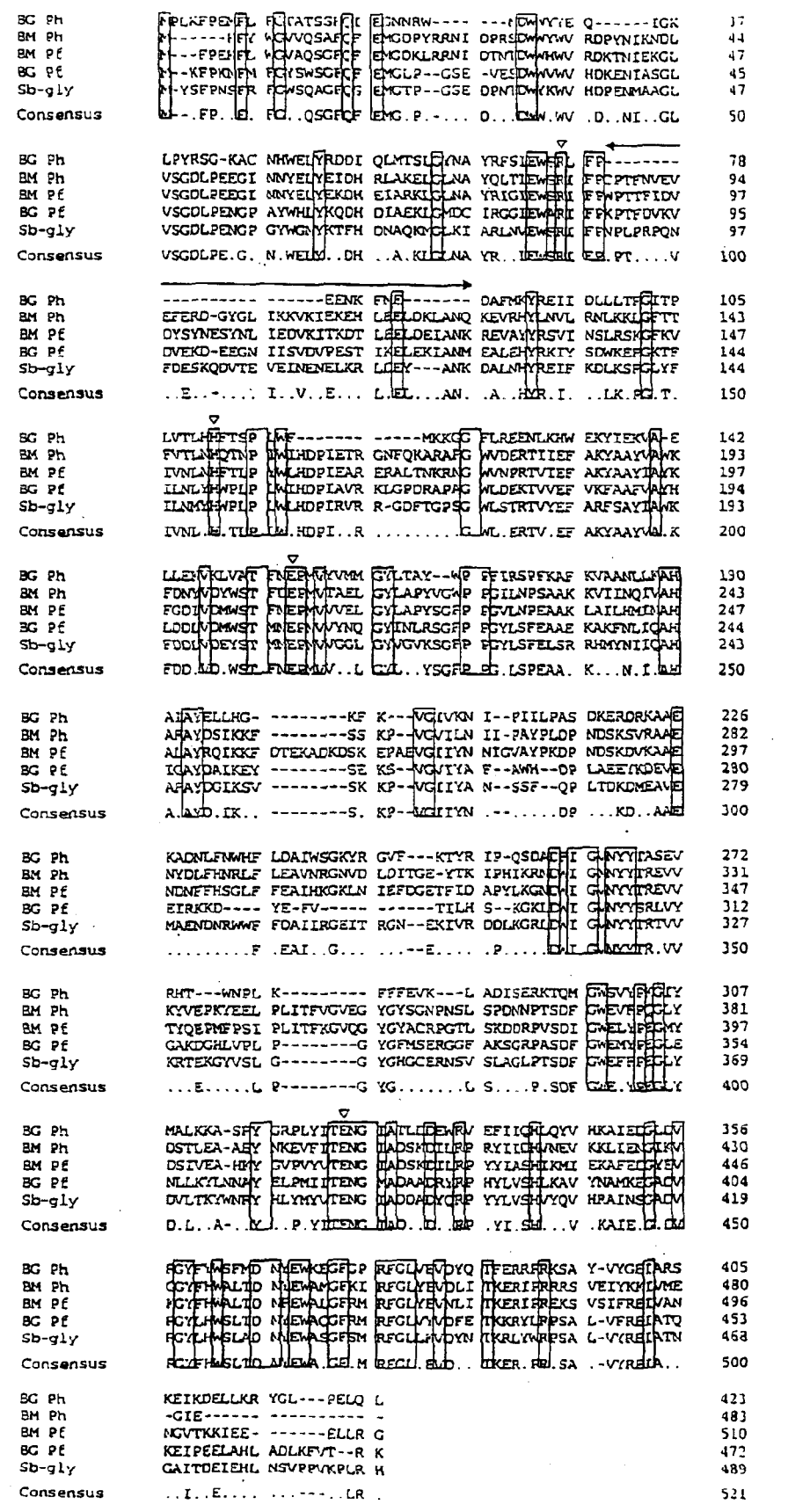

Henrissat proposed an alternate and complementary classification scheme for glycosyl hydrolases based on amino acid sequence similarities (24–26). For example, glycosyl hydrolase family 1 is composed of exo-acting, β-specific enzymes with similar amino acid sequences. The five β-glycosidases, including BGPh from the archaea domain (as shown in FIG. 5), belong to family 1. Some family 1 glycosyl hydrolases also have glycosyl transferase activities. The *S. solfataricus* β-glucosidase has been implicated in the glycosylation of membrane lipid components (27). Similarly, the enzymatic analysis of BMPf predicted its possible role in the synthesize of intracellular components including protein, membrane components, or other compounds (17). Since the localization of BGPh on *E. coli* membrane strongly indicates the intimate interaction of the enzyme and lipid components, the detection of BGPh on the *Pyrococcus* cell surface using antibody against the enzyme must be done to clarify its true function in the *Pyrococcus* cell.

The Structural Elements Responsible for Membrane Localization and the Conservation of Residues Forming the Active Site The sequence alignment among BGPh and four different β-glycosidases, whose biochemical characteristics have been reported (7, 17, 21–23), is shown in FIG. 5. According to the phylogenetic analysis based on the alignment, the tree has three branches: one corresponding to a β-glycosidase group that includes BGPf and Sβ-gly; another containing BMPh and BMPf, which were close to β-mannosidase. BGPh belongs to the third branch, located some distance from the first two branches. The polypeptide length of BGPh is also approximately 13% shorter than those of the other four β-glycosidases and might be one of the shortest sequences so far reported (8, 17, 18, 28). As shown in FIG. 5, the residues E155 and H111 of BGPh correspond to E206 and H150 as the putative acid/base catalyst in the Sβ-gly molecule (28, 29), whose steric structure has been reported (30). The residues E324 and R75 of BGPh correspond to E387, the nucleophile, and R79 in the spatial proximity of the nucleophile (28, 29). The complex structure of Bacillus polymixa β-glycosidase with the inhibitor gluconate has been reported (31). The BGPh residues, Q19, H111, N154, E155, Y267, E324, W362, E369, and W370 are completely conserved (FIG. 5) and correspond to the B. polymixa β-glycosidase residues, Q20, H121, N165, E166, Y296, E352, W398, E405, and W406, which form the intimate interaction with the inhibitor (31).

Figure 6:
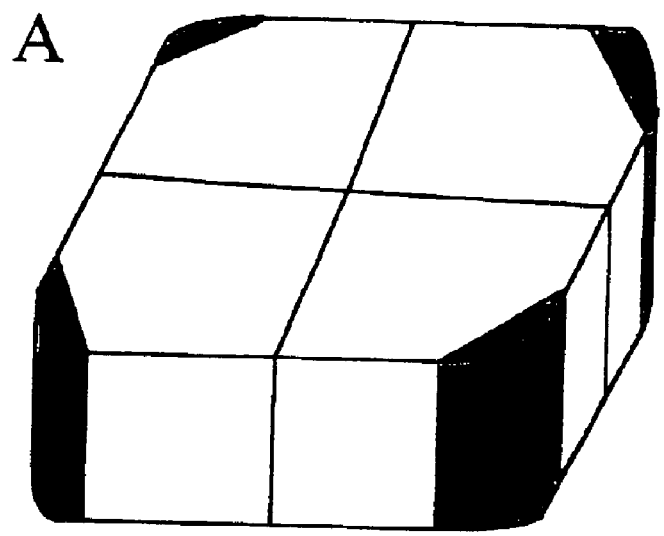
FIG. 6 shows illustrated location of the four hydrophilic edges on the tetragonal structure of Sβ-gly (30) and the four hydrophobic areas exposed by removing the hydrophilic loops forming the edges. (A) The tetragonal arrengement with the hydrophilic edges (blue) (B) The tetragonal arrengement with a hydrophobic surface (red) created by the deletion of the hydrophilic loops, shielding barrel helices 3 and 4 from solvent.
Figure 6:
Figure 6:
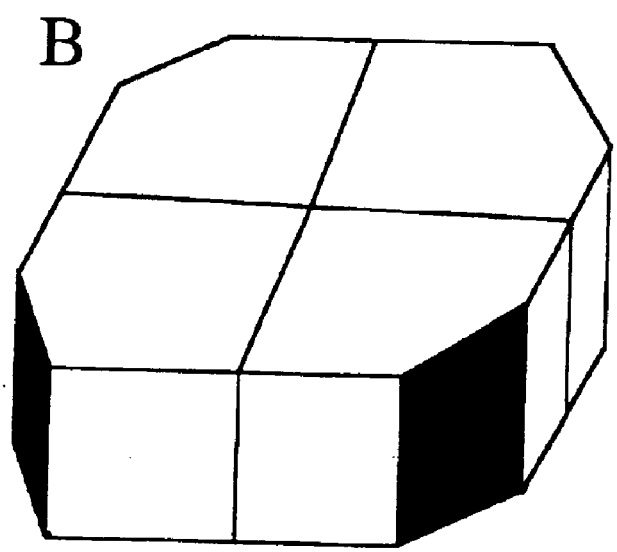

To understand the localization mechanism of BGPh to the membrane, a major structural difference between BGPh and the other soluble β-glycosidases was analyzed using the sequence alignment and the steric structure of Sβ-gly (30). The Sβ-gly molecule has the classic $(\beta\alpha)_8$ barrel fold first seen in the structure of triose phosphate isomerase (32). For BGPh, the prominent deletion of more than 30 residues was found after the 78th residue, as indicated in FIG. 5. The deletion region of BGPh corresponds to loops from the 89th to 125th residues of Sβ-gly, mainly shielding the helices 3 and 4 from solvent. The hydrophilic loops, which pack against the outer face of the barrel helices 3 and 4, were not present in the BGPh molecule. A tetrameric Sβ-gly structure has been reported, in which these loop regions were located at the four edges of regular tetragonal molecular arrangement (30). FIG. 6 illustrates the location of the four hydrophilic edges and four hydrophobic areas which appear following the removal of the hydrophilic loops. Since BGPh as well as Sβ-gly was proved to be tetramer by gel filtration using buffer containing 0.01% Triton X-100 (data not shown), the deletion of these hydrophilic loops probably results in the exposure of helices 3 and 4 to the solvent at the four edges of the tetrameric structure. The exposed hydrophobic areas might interact with lipid components to embed the molecule in the membrane.

Figure 7:
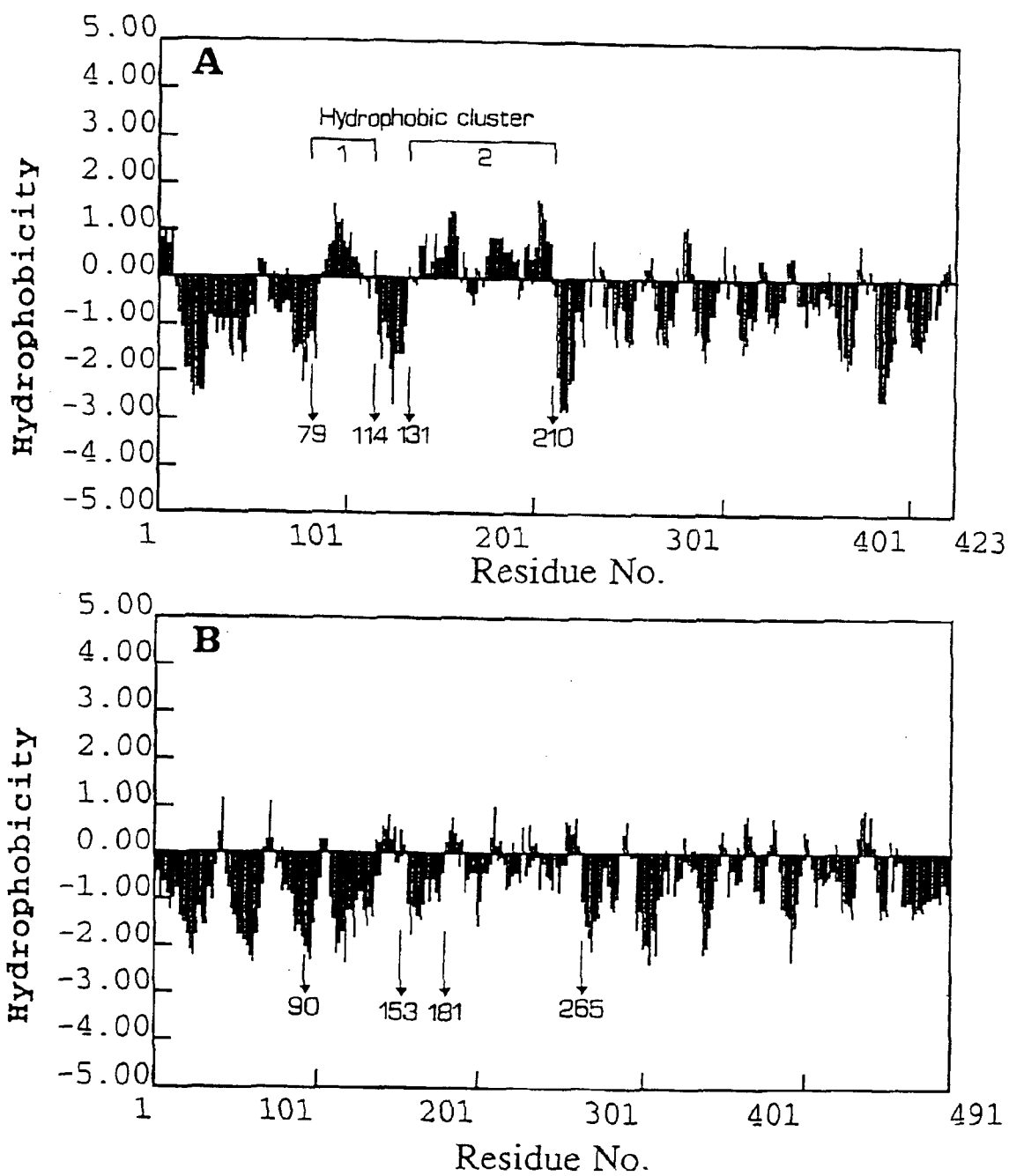
FIG. 7 shows a comparison of hydropacy profiles between BGPh and Sβ-gly. The panel (A) shows the hydropacy profile of BGPh and panel (B) shows the hydropacy profile of Sβ-gly. The arrows indicate the corresponding residue numbers. Two hydrophobic clusters are observed in BGPh but not in Sβ-gly.

The increased hydrophobicity at barrel helices 3 and 4 is also indicated by the comparison of the hydropacy plots of BGPh and Sβ-gly, as shown in FIG. 7. Two major hydrophobic clusters were observed in the region of BGPh between residues 79 and 210 corresponding to the region of Sβ-gly between residues 90 and 265. These residues form tertiary structures from the end of β-sheet 2 to the beginning of β-sheet 5 of the $(\beta\alpha)_8$ barrel fold (30). The first cluster was located between residues 79 to 114, forming a helix with a loop shortened by the deletion, α-helix 2, and β-sheet 3. The second cluster was present between residues 131 and 210, corresponding the barrel fold between a-helices 3 and 4 exposed to solvent. A hydrophilic module that might be important for enzyme orientation on the membrane was found between residues 114 to 131, corresponding to the hydrophilic helices at the molecule surface located between the β-strand and the α-helix in the third repeat of the barrel fold. The two hydrophobic clusters, but not the hydrophilic module, were lacking in the corresponding region of Sβ-gly (18).

A mechanism for the localization of BGPh is proposed here based on the possible hydrophobic interaction between the membrane and the exposed hydrophobic helices 3 and 4 at the four edges of the tetrameric structure exposed by the deletion of the hydrophilic loops. Furthermore, the mechanism is well supported by the hydropacy profile of BGPh, in which the hydrophobic cluster is formed by the barrel fold between a-helices 3 and 4. The exposed hydrophobic areas may lead the hydrophobic substrates to the active site and bind them there. However, further studies using the crystallographic analysis are needed for a more definitive description of the detailed mechanism for recognition of the hydrophobic aglycon part, including a long alkyl-chain.

As described above, the present invention provides a novel β-glycosidase. The β-glycosidase is stable under extreme conditions. Therefore, the β-glycosidase can be used to develop heterosaccharides with high optical purities.

REFERENCES

1. Cowan, D. A. (1992) The Archaebacteria: Biochemistry and Biotechnology (Danson M. J., Hough, D. W., and Lunt, G. G., eds.) pp. 149–170. Portland Press, London and Chapel Hill
2. Tricone, A., Nicolaus, B., Lama, L., and Gambacorta, A. (1993) Indian J. Chem. (Section B) 32, 25–29
3. Hudson, R. C., Schofield, L. R., Coolbear, T., Daniel, R. M., and Morgan, H. W. (1991) Biochem. J. 273, 645–650
4. Kume, S. and Fujio, Y. (1991) J. Gen. Appl. Microbiol. 37, 25–34
5. Tokatlidis, K., Dhurjati, P., Millet, J., Beguin, P., and Rossi, M. (1991) FEBS Lett. 282, 205–208
6. Toone, E. J., Simon, E. S., Bednarski, M. D., and Whitesides, G. M. (1989) Tetrahedron 45, 5365–5422
7. Tricone, A., Improta, R., Nucci, R., Rossi, M., and Gambacorta, A. (1994) Biocatalysis 10, 195–210
8. Kawarabayasi, Y., Sawada, M., Horikoshi, H., Haikawa, Y., Hino, Y., Yamamoto, S., Sekine, M., Baba, S., Kosugi, H., Hosoyama, A., Nagai, Y., Sakai, M., Ogura, K., Otsuka, R., Nakazawa, H., Takamiya, M., Ohfuku, Y., Funahashi, T., Tanaka, T., Kudoh, Y., Yamazaki, J., Kushida, N., Oguchi, A., Aoki, K., Yoshizawa, T., Nakamura, Y., Robb, F. T., Horikoshi, K., Masuchi, Y., Shizuya, H., and Kikuchi, H. (1998) DNA Res. 5, 55–76
9. Kawarabayasi, Y., Sawada, M., Horikoshi, H., Haikawa, Y., Hino, Y., Yamamoto, S., Sekine, M., Baba, S., Kosugi, H., Hosoyama, A., Nagai, Y., Sakai, M., Ogura, K., Otsuka, R., Nakazawa, H., Takamiya, M., Ohfuku, Y., Funahashi, T., Tanaka, T., Kudoh, Y., Yamazaki, J., Kushida, N., Oguchi, A., Aoki, K., Yoshizawa, T., Nakamura, Y., Robb, F. T., Horikoshi, K., Masuchi, Y., Shizuya, H., and Kikuchi, H. (1998) DNA Res. 5, 147–155
10. Kaneko, T., Tanaka, A., Sato, S., Kotani, H., Sazuka, T., Miyajima, N., Sugiura, M., and Tabata, S. (1995) DNA Res. 2, 153–166
11. Laemmli, U. K. (1970) Nature 227, 680–682
12. Sakada, M. andHiromi, K. (1976) J.Biochem. 80, 547–555
13. Matsui, I., Ishikawa, K., Matsui, E., Miyairi, S., Fukui, S., and Honda, K. (1991) J. Biochem. 109, 566–569
14. Matsui, I., Ishikawa, K., Matsui, E., Miyairi, S., Fukui, S., and Honda, K. (1992) FEBS Lett. 310, 216–218
15. Suganuma, T., Matsuno, R., Ohnishi, M., and Hiromi, K. (1978) J. Biochem. 84, 293–316
16. Hiromi, K. (1970) Biochem. Biophys. Res. Commun. 40, 1–6
17. Bauer, M. W., Bylina, E. J., Swanson, R. V., and Kelly, R. M. (1996) J. Biol. Chem. 271, 23749–23755
18. Cubellis, M. W., Rozzo, C., Montecucch, P., and Rossi, M. (1990) Gene 94, 89–94
19. Nei M. (1987) Molecular Evolutionary Genetics, pp. 293–298. Columbia University Press, New York, N.Y.
20. Kyte, J. and Doolittle, R. F. (1982) J. Mol. Biol. 157, 105–132
21. Nucci, R., Moracci, M., Vaccaro, C., Vespa, N., and Rossi, M. (1993) Biotechnol. Appl. Biochem. 17, 239–250
22. Kengen, S. W. M., Luesink, E. J., Stams, A. J. M., and Zehnder, A. J. B. (1993) Eur. J. Biochem. 213, 305–312
23. Bauer, M. W. and Kelly, R. M. (1998) Biochemistry 37, 17170–17178
24. Henrissat, B. (1991) Biochem. J. 280, 309–316

25. Henrissat, B. and Bairoch, A. (1993) Biochem. J. 293, 781–788
26. Henrissat, B. and Bairoch, A. (1996) Biochem. J. 316, 695–696
27. Grogan, D. W. (1991) Appl. Environ. Microbiol. 57, 1644–1649
28. Febbraio, F., Barone, R., D'Auria, S., Rocci, M., and Nucci, R. (1997) Biochemistry 36, 3068–3075
29. Moracci, M., Trincone, A., Perugino, G., Ciaramella, M., and Rossi, M. (1998) Biochemistry 37, 17262–17270
30. Aguilar, C. F., Sanderson, I., Moracci, M., Ciaramella, M., Nucci, R., Rocci, M., and Pearl, L. H. (1997) J. Mol. Biol. 271, 789–802
31. Sanz-Aparicio, J., Hermoso, J. A., Martinez-Ripollo, M., Lequerica, J. L., and Polaina, J. (1998) J. Mol. Biol. 275, 491–502
32. Banner, D. W., Bloomer, A. C., Petsko, G. A., Phillips, D. C., Pogson, C. I., Wilson, I. A., Corran, P. H., Furth, A. J., Milman, J. D., Offord, R. E., Priddle, J. D., and Waley, S. G. (1975) Nature 255, 609–614

All publications, patents and patent applications cited herein are incorporated herein by reference in their entity.

The invention has been described in detail with reference to various embodiments, and it will now be apparent from the foregoing to those skilled in the art that changes and modifications may be made without departing from the invention in its broader aspects, and it is the invention, therefore, in the appended claims to cover all such changes and modifications as fall within the true spirit of the invention.

The following is information on sequences described herein:

What is claimed is:

1. A process for the hydrolysis of a β-glycoside having a long alkyl chain at the reducing end, comprising contacting the β-glucoside with a thermophilic enzyme comprising the amino acid sequence of SEQ ID NO: 2, wherein the long alkyl chain is an alkyl group having carbon atoms of 8 or more.

2. The process of claim 1, wherein the hydrolysis is carried out at a temperature of 85° C. or higher.

3. The process of claim 1, wherein the hydrolysis is carried out at a temperature of 100° C. or higher.

4. A method for using a thermophilic enzyme as a β-glycosidase, comprising the following steps:
   (a) providing an enzyme, wherein the enzyme comprises four subunits to form a tetramer, wherein each subunit of the tetramer comprises a sequence as set forth in SEQ ID NO:2; and
   (b) contacting the tetrameric enzyme with a β-glucoside comprising a long alkyl chain under conditions wherein the enzyme functions as a β-glycosidase, wherein the long alkyl chain comprises 8 or more carbon atoms.

5. The method of claim 4, wherein the enzyme has a high affinity to a β-glucoside comprising a long alkyl chain.

6. The method of claim 4, wherein the β-glucoside having a long alkyl chain is selected from the group consisting of n-Dodecyl-β-D-Glcp and n-Octyl-β-D-Glcp.

7. The method of claim 4, wherein the function comprises synthesis of an oligosaccharide or a heterosaccharide with optical purity.

8. The method of claim 4, wherein the conditions comprise temperatures selected from the group consisting of 90° C. or higher and 100° C. or higher.

9. The method of claim 4, wherein the conditions comprise an organic solvent.

10. The method of claim 4, wherein the enzyme is encoded by a nucleotide sequence comprising SEQ ID NO:1.

11. The method of claim 4, wherein the enzyme is encoded by a nucleotide sequence capable of hybridizing to SEQ ID NO:1, or its complement, under high stringent conditions of 6×SSC and 30% formamide at 42° C., wherein the hybridization further comprises a washing step at 0.1× SSC and 0% formamaide at 62° C.

12. The process of claim 1, wherein the β-glycoside is contacted with the enzyme in 50 mM phosphate buffer (pH 6.0) with 0.1% Triton X-100 and 0.3 M NaCl at 90° C.

* * * * *

SEQUENCE LISTING

<160> NUMBER OF SEQ ID NOS: 9

<210> SEQ ID NO 1
<211> LENGTH: 1269
<212> TYPE: DNA
<213> ORGANISM: Pyrococcus horikoshii
<220> FEATURE:
<221> NAME/KEY: CDS
<222> LOCATION: (1)...(1269)

<400> SEQUENCE: 1

```
atg ccg ctg aaa ttc ccg gaa atg ttt ctc ttt ggt acc gca aca tca      48
Met Pro Leu Lys Phe Pro Glu Met Phe Leu Phe Gly Thr Ala Thr Ser
1               5                  10                  15 tcc cat cag ata gag gga aat aat aga tgg aat gat tgg tgg tac tat      96
Ser His Gln Ile Glu Gly Asn Asn Arg Trp Asn Asp Trp Trp Tyr Tyr
                20                  25                  30 gag cag att gga aag ctc ccc tac aga tct ggt aag gct tgc aat cac     144
Glu Gln Ile Gly Lys Leu Pro Tyr Arg Ser Gly Lys Ala Cys Asn His
            35                  40                  45 tgg gaa ctt tac agg gat gat att cag cta atg acc agc ttg ggc tat     192
Trp Glu Leu Tyr Arg Asp Asp Ile Gln Leu Met Thr Ser Leu Gly Tyr
        50                  55                  60 aat gct tat agg ttc tcc ata gag tgg agc agg cta ttc cca gag gaa     240
Asn Ala Tyr Arg Phe Ser Ile Glu Trp Ser Arg Leu Phe Pro Glu Glu
65                  70                  75                  80 aat aaa ttt aat gaa gat gct ttc atg aaa tac cgg gag att ata gac     288
Asn Lys Phe Asn Glu Asp Ala Phe Met Lys Tyr Arg Glu Ile Ile Asp
                85                  90                  95 ttg tta ttg acg aga ggt ata act ccc ctg gtg acc cta cac cac ttt     336
Leu Leu Leu Thr Arg Gly Ile Thr Pro Leu Val Thr Leu His His Phe
            100                 105                 110 act agc cct ctc tgg ttc atg aag aaa ggt ggc ttc ctt agg gag gag     384
Thr Ser Pro Leu Trp Phe Met Lys Lys Gly Gly Phe Leu Arg Glu Glu
        115                 120                 125 aac cta aaa cat tgg gaa aag tac ata gaa aag gtt gct gag ctt tta     432
Asn Leu Lys His Trp Glu Lys Tyr Ile Glu Lys Val Ala Glu Leu Leu
    130                 135                 140 gaa aaa gtt aaa cta gta gct acc ttc aat gag ccg atg gta tac gta     480
Glu Lys Val Lys Leu Val Ala Thr Phe Asn Glu Pro Met Val Tyr Val
145                 150                 155                 160 atg atg gga tat cta acg gct tat tgg ccc cca ttc att agg agt cca     528
Met Met Gly Tyr Leu Thr Ala Tyr Trp Pro Pro Phe Ile Arg Ser Pro
                165                 170                 175
```

```
ttt aag gcc ttt aag gta gct gca aac ctg ctt aaa gct cac gca att      576
Phe Lys Ala Phe Lys Val Ala Ala Asn Leu Leu Lys Ala His Ala Ile
        180                 185                 190 gcc tat gaa ctt ctt cat ggg aaa ttc aaa gtt gga atc gta aag aat      624
Ala Tyr Glu Leu Leu His Gly Lys Phe Lys Val Gly Ile Val Lys Asn
            195                 200                 205 att ccc ata ata ctc cca gcg agt gac aag gag agg gat aga aaa gcc      672
Ile Pro Ile Ile Leu Pro Ala Ser Asp Lys Glu Arg Asp Arg Lys Ala
210                 215                 220 gct gag aaa gct gat aat tta ttt aac tgg cac ttt ttg gat gcg ata      720
Ala Glu Lys Ala Asp Asn Leu Phe Asn Trp His Phe Leu Asp Ala Ile
225                 230                 235                 240 tgg agt ggg aaa tac aga ggg gta ttt aaa aca tat agg att ccc caa      768
Trp Ser Gly Lys Tyr Arg Gly Val Phe Lys Thr Tyr Arg Ile Pro Gln
                245                 250                 255 agt gac gca gat ttc att ggg gtt aac tat tac acg gcc agc gaa gta      816
Ser Asp Ala Asp Phe Ile Gly Val Asn Tyr Tyr Thr Ala Ser Glu Val
            260                 265                 270 agg cat act tgg aat cct tta aaa ttc ttc ttt gag gtg aaa tta gcg      864
Arg His Thr Trp Asn Pro Leu Lys Phe Phe Phe Glu Val Lys Leu Ala
        275                 280                 285 gat att agc gag agg aag act caa atg gga tgg agc gtt tat cca aaa      912
Asp Ile Ser Glu Arg Lys Thr Gln Met Gly Trp Ser Val Tyr Pro Lys
290                 295                 300 gga ata tac atg gcc ctt aaa aaa gct tcc agg tat gga agg cct ctt      960
Gly Ile Tyr Met Ala Leu Lys Lys Ala Ser Arg Tyr Gly Arg Pro Leu
305                 310                 315                 320 tat att acg gaa aac gga ata gcg acg ctt gat gat gaa tgg aga gtg     1008
Tyr Ile Thr Glu Asn Gly Ile Ala Thr Leu Asp Asp Glu Trp Arg Val
                325                 330                 335 gaa ttc ata att caa cac ctc caa tac gtt cat aag gct atc gaa gac     1056
Glu Phe Ile Ile Gln His Leu Gln Tyr Val His Lys Ala Ile Glu Asp
            340                 345                 350 ggc ctg gat gta aga ggt tac ttc tat tgg tca ttt atg gat aac tac     1104
Gly Leu Asp Val Arg Gly Tyr Phe Tyr Trp Ser Phe Met Asp Asn Tyr
        355                 360                 365 gag tgg aaa gag ggg ttt ggg cct aga ttt ggc cta gtg gaa gtt gat     1152
Glu Trp Lys Glu Gly Phe Gly Pro Arg Phe Gly Leu Val Glu Val Asp
370                 375                 380 tat caa acc ttc gag aga agg ccc agg aag agt gct tac gta tac gga     1200
Tyr Gln Thr Phe Glu Arg Arg Pro Arg Lys Ser Ala Tyr Val Tyr Gly
385                 390                 395                 400 gaa att gca aga agt aag gaa ata aag gat gag cta tta aag aga tat     1248
Glu Ile Ala Arg Ser Lys Glu Ile Lys Asp Glu Leu Leu Lys Arg Tyr
                405                 410                 415 ggc cta cca gaa ctt caa ctt                                         1269
Gly Leu Pro Glu Leu Gln Leu
                420

<210> SEQ ID NO 2
<211> LENGTH: 423
<212> TYPE: PRT
<213> ORGANISM: Pyrococcus horikoshii

<400> SEQUENCE: 2

Met Pro Leu Lys Phe Pro Glu Met Phe Leu Phe Gly Thr Ala Thr Ser
  1               5                  10                  15

Ser His Gln Ile Glu Gly Asn Asn Arg Trp Asn Asp Trp Trp Tyr Tyr
             20                  25                  30
```

```
Glu Gln Ile Gly Lys Leu Pro Tyr Arg Ser Gly Lys Ala Cys Asn His
        35                  40                  45
Trp Glu Leu Tyr Arg Asp Asp Ile Gln Leu Met Thr Ser Leu Gly Tyr
 50                  55                  60
Asn Ala Tyr Arg Phe Ser Ile Glu Trp Ser Arg Leu Phe Pro Glu Glu
65                  70                  75                  80
Asn Lys Phe Asn Glu Asp Ala Phe Met Lys Tyr Arg Glu Ile Ile Asp
                85                  90                  95
Leu Leu Leu Thr Arg Gly Ile Thr Pro Leu Val Thr Leu His His Phe
            100                 105                 110
Thr Ser Pro Leu Trp Phe Met Lys Lys Gly Phe Leu Arg Glu Glu
            115                 120                 125
Asn Leu Lys His Trp Glu Lys Tyr Ile Glu Lys Val Ala Glu Leu Leu
130                 135                 140
Glu Lys Val Lys Leu Val Ala Thr Phe Asn Glu Pro Met Val Tyr Val
145                 150                 155                 160
Met Met Gly Tyr Leu Thr Ala Tyr Trp Pro Pro Phe Ile Arg Ser Pro
                165                 170                 175
Phe Lys Ala Phe Lys Val Ala Ala Asn Leu Leu Lys Ala His Ala Ile
            180                 185                 190
Ala Tyr Glu Leu Leu His Gly Lys Phe Lys Val Gly Ile Val Lys Asn
            195                 200                 205
Ile Pro Ile Ile Leu Pro Ala Ser Asp Lys Glu Arg Asp Arg Lys Ala
            210                 215                 220
Ala Glu Lys Ala Asp Asn Leu Phe Asn Trp His Phe Leu Asp Ala Ile
225                 230                 235                 240
Trp Ser Gly Lys Tyr Arg Gly Val Phe Lys Thr Tyr Arg Ile Pro Gln
                245                 250                 255
Ser Asp Ala Asp Phe Ile Gly Val Asn Tyr Tyr Thr Ala Ser Glu Val
            260                 265                 270
Arg His Thr Trp Asn Pro Leu Lys Phe Phe Glu Val Lys Leu Ala
            275                 280                 285
Asp Ile Ser Glu Arg Lys Thr Gln Met Gly Trp Ser Val Tyr Pro Lys
290                 295                 300
Gly Ile Tyr Met Ala Leu Lys Lys Ala Ser Arg Tyr Gly Arg Pro Leu
305                 310                 315                 320
Tyr Ile Thr Glu Asn Gly Ile Ala Thr Leu Asp Asp Glu Trp Arg Val
                325                 330                 335
Glu Phe Ile Ile Gln His Leu Gln Tyr Val His Lys Ala Ile Glu Asp
            340                 345                 350
Gly Leu Asp Val Arg Gly Tyr Phe Tyr Trp Ser Phe Met Asp Asn Tyr
            355                 360                 365
Glu Trp Lys Glu Gly Phe Gly Pro Arg Phe Gly Leu Val Glu Val Asp
            370                 375                 380
Tyr Gln Thr Phe Glu Arg Arg Pro Arg Lys Ser Ala Tyr Val Tyr Gly
385                 390                 395                 400
Glu Ile Ala Arg Ser Lys Glu Ile Lys Asp Glu Leu Leu Lys Arg Tyr
                405                 410                 415
Gly Leu Pro Glu Leu Gln Leu
            420

<210> SEQ ID NO 3
<211> LENGTH: 57
<212> TYPE: DNA
```

<213> ORGANISM: Artificial Sequence
<220> FEATURE:
<223> OTHER INFORMATION: An upper primer designed to create the NdeI site.

<400> SEQUENCE: 3
taagaaggag atatacatat gccgctgaaa ttcccggaaa tgtttctctt tggtacc    57

<210> SEQ ID NO 4
<211> LENGTH: 46
<212> TYPE: DNA
<213> ORGANISM: Artificial Sequence
<220> FEATURE:
<223> OTHER INFORMATION: A lower primer designed to create the BamHI site.

<400> SEQUENCE: 4
tttactgcag agaggatccc taatcctaaa gttgaagttc tggtag    46

<210> SEQ ID NO 5
<211> LENGTH: 483
<212> TYPE: PRT
<213> ORGANISM: Pyrococcus horikoshii

<400> SEQUENCE: 5

```
Met Lys Phe Tyr Trp Gly Val Val Gln Ser Ala Phe Gln Phe Glu Met
 1               5                  10                  15

Gly Asp Pro Tyr Arg Arg Asn Ile Asp Pro Arg Ser Asp Trp Trp Tyr
                20                  25                  30

Trp Val Arg Asp Pro Tyr Asn Ile Lys Asn Asp Leu Val Ser Gly Asp
            35                  40                  45

Leu Pro Glu Glu Gly Ile Asn Asn Tyr Glu Leu Tyr Glu Ile Asp His
    50                  55                  60

Arg Leu Ala Lys Glu Leu Gly Leu Asn Ala Tyr Gln Leu Thr Ile Glu
65                  70                  75                  80

Trp Ser Arg Ile Phe Pro Cys Pro Thr Phe Asn Val Glu Val Glu Phe
                85                  90                  95

Glu Arg Asp Asx Tyr Gly Leu Ile Lys Lys Val Lys Ile Glu Lys Glu
                100                 105                 110

His Leu Glu Glu Leu Asp Lys Leu Ala Asn Gln Lys Glu Val Arg His
            115                 120                 125

Tyr Leu Asn Val Leu Arg Asn Leu Lys Lys Leu Gly Phe Thr Thr Phe
    130                 135                 140

Val Thr Leu Asn His Gln Thr Asn Pro Ile Trp Ile His Asp Pro Ile
145                 150                 155                 160

Glu Thr Arg Gly Asn Phe Gln Lys Ala Arg Ala Pro Gly Trp Val Asp
                165                 170                 175

Glu Arg Thr Ile Ile Glu Phe Ala Lys Tyr Ala Ala Tyr Val Ala Trp
            180                 185                 190

Lys Phe Asp Asn Tyr Val Asp Tyr Trp Ser Thr Phe Asp Glu Pro Met
    195                 200                 205

Val Thr Ala Glu Leu Gly Tyr Leu Ala Pro Tyr Val Gly Trp Pro Pro
    210                 215                 220

Gly Ile Leu Asn Pro Ser Ala Ala Lys Lys Val Ile Ile Asn Gln Ile
225                 230                 235                 240

Val Ala His Ala Pro Ala Tyr Asp Ser Ile Lys Lys Phe Ser Ser Lys
                245                 250                 255

Pro Val Gly Val Ile Leu Asn Ile Ile Pro Ala Tyr Pro Leu Asp Pro
```

```
                  260                 265                 270
Asn Asp Ser Lys Ser Val Arg Ala Ala Glu Asn Tyr Asp Leu Phe His
                275                 280                 285
Asn Arg Leu Phe Leu Glu Ala Val Asn Arg Gly Asn Val Asp Leu Asp
            290                 295                 300
Ile Thr Gly Glu Tyr Thr Lys Ile Pro His Ile Lys Arg Asn Asp Trp
305                 310                 315                 320
Ile Gly Asn Asn Tyr Tyr Thr Arg Glu Val Lys Tyr Val Glu Pro
                325                 330                 335
Lys Tyr Glu Glu Leu Pro Leu Ile Thr Phe Val Gly Val Glu Gly Tyr
            340                 345                 350
Gly Tyr Ser Gly Asn Pro Asn Ser Leu Ser Pro Asp Asn Asn Pro Thr
            355                 360                 365
Ser Asp Phe Gly Trp Glu Val Phe Pro Gln Gly Leu Tyr Asp Ser Thr
        370                 375                 380
Leu Glu Ala Ala Glu Tyr Asn Lys Glu Val Phe Ile Thr Glu Asn Gly
385                 390                 395                 400
Ile Ala Asp Ser Lys Asp Ile Leu Arg Pro Arg Tyr Ile Ile Asp His
                405                 410                 415
Val Asn Glu Val Lys Lys Leu Ile Glu Asn Gly Ile Lys Val Gly Gly
            420                 425                 430
Tyr Phe His Trp Ala Leu Thr Asp Asn Tyr Glu Trp Ala Met Gly Phe
            435                 440                 445
Lys Ile Arg Phe Gly Leu Tyr Glu Val Asp Leu Ile Thr Lys Glu Arg
        450                 455                 460
Ile Pro Arg Arg Ser Val Glu Ile Tyr Lys Lys Ile Val Met Glu
465                 470                 475                 480
Gly Ile Glu

<210> SEQ ID NO 6
<211> LENGTH: 510
<212> TYPE: PRT
<213> ORGANISM: Pyrococcus furiosus

<400> SEQUENCE: 6

Met Phe Pro Glu Met Phe Leu Trp Gly Val Ala Gln Ser Gly Phe Gln
  1               5                  10                  15
Phe Glu Met Gly Asp Lys Leu Arg Arg Asn Ile Asp Thr Asn Thr Asp
                20                  25                  30
Trp Trp His Trp Val Arg Asp Lys Thr Asn Ile Glu Lys Gly Leu Val
            35                  40                  45
Ser Gly Asp Leu Pro Glu Glu Gly Ile Asn Asn Tyr Glu Leu Tyr Glu
        50                  55                  60
Lys Asp His Glu Ile Ala Arg Lys Leu Gly Leu Asn Ala Tyr Arg Ile
 65                  70                  75                  80
Gly Ile Glu Trp Ser Arg Ile Phe Pro Trp Pro Thr Thr Phe Ile Asp
                85                  90                  95
Val Asp Tyr Ser Tyr Asn Glu Ser Tyr Asn Leu Ile Glu Asp Val Lys
                100                 105                 110
Ile Thr Lys Asp Thr Leu Glu Glu Leu Asp Glu Ile Ala Asn Lys Arg
            115                 120                 125
Glu Val Ala Tyr Tyr Arg Ser Val Ile Asn Ser Leu Arg Ser Lys Gly
        130                 135                 140
Phe Lys Val Ile Val Asn Leu Asn His Phe Thr Leu Pro Tyr Trp Asp
```

```
            145                 150                 155                 160
His Asp Pro Ile Glu Ala Arg Glu Arg Ala Leu Thr Asn Lys Arg Asn
                165                 170                 175

Gly Trp Val Asn Pro Arg Thr Val Ile Glu Phe Ala Lys Tyr Ala Ala
            180                 185                 190

Tyr Ile Ala Tyr Lys Phe Gly Asp Ile Val Asp Met Trp Ser Thr Phe
            195                 200                 205

Asn Glu Pro Met Val Val Glu Leu Gly Tyr Leu Ala Pro Tyr Ser
            210                 215                 220

Gly Phe Pro Pro Gly Val Leu Asn Pro Glu Ala Ala Lys Leu Ala Ile
225                 230                 235                 240

Leu His Met Ile Asn Ala His Ala Leu Ala Tyr Arg Gln Ile Lys Lys
                245                 250                 255

Phe Asp Thr Glu Lys Ala Asp Lys Asp Ser Lys Glu Pro Ala Glu Val
            260                 265                 270

Gly Ile Ile Tyr Asn Asn Ile Gly Val Ala Tyr Pro Lys Asp Pro Asn
            275                 280                 285

Asp Ser Lys Asp Val Lys Ala Ala Glu Asn Asp Asn Phe Phe His Ser
290                 295                 300

Gly Leu Phe Phe Glu Ala Ile His Lys Gly Lys Leu Asn Ile Glu Phe
305                 310                 315                 320

Asp Gly Glu Thr Phe Ile Asp Ala Pro Tyr Leu Lys Gly Asn Asp Trp
                325                 330                 335

Ile Gly Met Asn Tyr Tyr Thr Arg Glu Val Val Thr Tyr Gln Glu Pro
            340                 345                 350

Met Phe Pro Ser Ile Pro Leu Ile Thr Phe Lys Gly Val Gln Gly Tyr
            355                 360                 365

Gly Tyr Ala Cys Arg Pro Gly Thr Gln Ser Lys Asp Asp Arg Pro Val
            370                 375                 380

Ser Asp Ile Gly Trp Glu Leu Tyr Pro Glu Gly Met Tyr Asp Ser Ile
385                 390                 395                 400

Val Glu Ala His Lys Tyr Gly Val Pro Val Tyr Val Thr Glu Asn Gly
                405                 410                 415

Ile Ala Asp Ser Lys Asp Ile Leu Arg Pro Tyr Tyr Ile Ala Ser His
            420                 425                 430

Ile Lys Met Ile Glu Lys Ala Phe Glu Asp Gly Tyr Glu Val Lys Gly
            435                 440                 445

Tyr Phe His Trp Ala Leu Thr Asp Asn Phe Glu Trp Ala Leu Gly Phe
            450                 455                 460

Arg Met Arg Phe Gly Leu Tyr Glu Val Asn Leu Ile Thr Lys Glu Arg
465                 470                 475                 480

Ile Pro Arg Glu Lys Ser Val Ser Ile Phe Arg Glu Ile Val Ala Asn
                485                 490                 495

Asn Gly Val Thr Lys Lys Ile Glu Glu Leu Leu Arg Gly
                500                 505                 510

<210> SEQ ID NO 7
<211> LENGTH: 472
<212> TYPE: PRT
<213> ORGANISM: Pyrococcus furiosus

<400> SEQUENCE: 7

Met Lys Phe Pro Lys Met Phe Met Phe Gly Tyr Ser Trp Ser Gly Pro
1               5                   10                  15
```

-continued

```
Gln Phe Glu Met Gly Leu Pro Gly Ser Glu Val Ser Asp Trp Trp
             20                  25                  30
Val Trp Val His Asp Lys Glu Asn Ile Ala Ser Gly Leu Val Ser Gly
         35                  40                  45
Asp Leu Pro Glu Asn Gly Pro Ala Tyr Trp His Ile Tyr Lys Gln Asp
     50                  55                  60
His Asp Ile Ala Glu Lys Leu Gly Met Asp Cys Ile Arg Gly Gly Ile
 65                  70                  75                  80
Glu Trp Ala Arg Ile Phe Pro Lys Pro Thr Phe Asp Val Lys Val Asp
                 85                  90                  95
Val Glu Lys Asp Glu Gly Asn Ile Ile Ser Val Asp Val Pro Glu
             100                 105                 110
Ser Thr Ile Lys Glu Leu Glu Lys Ile Ala Asn Met Glu Ala Leu Glu
             115                 120                 125
His Tyr Arg Lys Ile Tyr Ser Asp Trp Lys Glu Pro Gly Lys Thr Phe
         130                 135                 140
Ile Leu Asn Leu Tyr His Trp Pro Leu Pro Leu Trp Ile His Asp Pro
145                 150                 155                 160
Ile Ala Val Arg Lys Leu Gly Pro Asp Arg Ala Pro Ala Gly Trp Leu
                 165                 170                 175
Asp Glu Lys Thr Val Val Glu Phe Val Lys Phe Ala Ala Phe Val Ala
             180                 185                 190
Tyr His Leu Asp Asp Leu Val Asp Met Trp Ser Thr Met Met Glu Pro
         195                 200                 205
Met Val Val Tyr Asn Gln Gly Tyr Ile Asn Leu Arg Ser Gly Phe Pro
     210                 215                 220
Pro Gly Tyr Leu Ser Phe Glu Ala Ala Glu Lys Ala Lys Phe Asn Leu
225                 230                 235                 240
Ile Gln Ala His Ile Gly Ala Tyr Asp Ala Ile Lys Glu Tyr Ser Glu
                 245                 250                 255
Lys Ser Val Gly Val Ile Tyr Ala Phe Ala Trp His Asp Pro Leu Ala
             260                 265                 270
Glu Glu Tyr Lys Asp Glu Val Glu Ile Arg Lys Lys Asp Tyr Glu
         275                 280                 285
Phe Val Thr Ile Leu His Ser Lys Gly Lys Leu Asp Trp Ile Gly Met
     290                 295                 300
Asn Tyr Tyr Ser Arg Leu Val Tyr Gly Ala Lys Asp Gly His Leu Val
305                 310                 315                 320
Pro Leu Pro Gly Tyr Gly Phe Met Ser Glu Arg Gly Phe Ala Lys
                 325                 330                 335
Ser Gly Arg Pro Ala Ser Asp Phe Gly Trp Glu Met Tyr Pro Glu Gly
             340                 345                 350
Leu Glu Asn Leu Leu Lys Tyr Leu Asn Asn Ala Tyr Glu Leu Pro Met
         355                 360                 365
Ile Ile Thr Glu Asn Gly Met Ala Asp Ala Asp Arg Tyr Arg Pro
     370                 375                 380
His Tyr Leu Val Ser His Leu Lys Ala Val Tyr Asn Ala Met Lys Glu
385                 390                 395                 400
Gly Ala Asp Val Arg Gly Tyr Leu His Trp Ser Leu Thr Asp Asn Tyr
                 405                 410                 415
Glu Trp Ala Gln Gly Phe Arg Met Arg Phe Gly Leu Val Tyr Val Asp
             420                 425                 430
Phe Glu Thr Lys Lys Arg Tyr Leu Arg Pro Ser Ala Leu Val Phe Arg
```

-continued

```
                435                 440                 445
Glu Ile Ala Thr Gln Lys Glu Ile Pro Glu Glu Leu Ala His Leu Ala
    450                 455                 460

Asp Leu Lys Phe Val Thr Arg Lys
465                 470

<210> SEQ ID NO 8
<211> LENGTH: 489
<212> TYPE: PRT
<213> ORGANISM: Sulfolobus solfataricus

<400> SEQUENCE: 8

Met Tyr Ser Phe Pro Asn Ser Phe Arg Phe Gly Trp Ser Gln Ala Gly
  1               5                  10                  15

Phe Gln Ser Glu Met Gly Thr Pro Gly Ser Glu Asp Pro Asn Thr Asp
                 20                  25                  30

Trp Tyr Lys Trp Val His Asp Pro Glu Asn Met Ala Ala Gly Leu Val
             35                  40                  45

Ser Gly Asp Leu Pro Glu Asn Gly Pro Gly Tyr Trp Gly Met Tyr Lys
         50                  55                  60

Thr Phe His Asp Asn Ala Gln Lys Met Gly Leu Lys Ile Ala Arg Leu
 65                  70                  75                  80

Asn Val Glu Trp Ser Arg Ile Phe Pro Asn Pro Leu Pro Arg Pro Gln
                 85                  90                  95

Asn Phe Asp Glu Ser Lys Gln Asp Val Thr Glu Val Glu Ile Asn Glu
            100                 105                 110

Asn Glu Leu Lys Arg Leu Asp Glu Tyr Ala Asn Lys Asp Ala Leu Asn
        115                 120                 125

His Tyr Arg Glu Ile Phe Lys Asp Leu Lys Ser Pro Gly Leu Tyr Phe
    130                 135                 140

Ile Leu Asn Met Tyr His Trp Pro Leu Pro Leu Trp Leu His Asp Pro
145                 150                 155                 160

Ile Arg Val Arg Arg Gly Asp Phe Thr Gly Pro Ser Gly Trp Leu Ser
                165                 170                 175

Thr Arg Thr Val Tyr Glu Phe Ala Arg Phe Ser Ala Tyr Ile Ala Trp
            180                 185                 190

Lys Phe Asp Asp Leu Val Asp Glu Tyr Ser Thr Met Met Glu Pro Met
        195                 200                 205

Val Val Gly Gly Leu Gly Tyr Val Gly Val Lys Ser Gly Phe Pro Pro
    210                 215                 220

Gly Tyr Leu Ser Phe Glu Leu Ser Arg Arg His Met Tyr Asn Ile Ile
225                 230                 235                 240

Gln Ala His Ala Arg Ala Tyr Asp Gly Ile Lys Ser Val Ser Lys Lys
                245                 250                 255

Pro Val Gly Ile Ile Tyr Ala Asn Ser Ser Phe Gln Pro Leu Thr Asp
            260                 265                 270

Lys Asp Met Glu Ala Val Glu Met Ala Glu Asn Asp Asn Arg Trp Trp
        275                 280                 285

Phe Phe Asp Ala Ile Ile Arg Gly Glu Ile Thr Arg Gly Asn Glu Lys
    290                 295                 300

Ile Val Arg Asp Asp Leu Lys Gly Arg Leu Asp Trp Ile Gly Met Asn
305                 310                 315                 320

Tyr Tyr Thr Arg Thr Val Val Lys Arg Thr Glu Lys Gly Tyr Val Ser
                325                 330                 335
```

-continued

```
Leu Gly Gly Tyr Gly His Gly Cys Glu Arg Asn Ser Val Ser Leu Ala
            340                 345                 350

Gly Leu Pro Thr Ser Asp Phe Gly Trp Glu Phe Pro Glu Gly Leu
        355                 360                 365

Tyr Asp Val Leu Thr Lys Tyr Trp Asn Arg Tyr His Leu Tyr Met Tyr
    370                 375                 380

Val Thr Glu Asn Gly Ile Ala Asp Asp Ala Asp Tyr Gln Arg Pro Tyr
385                 390                 395                 400

Tyr Leu Val Ser His Val Tyr Gln Val His Arg Ala Ile Asn Ser Gly
                405                 410                 415

Ala Asp Val Arg Gly Tyr Leu His Trp Ser Leu Ala Asp Asn Tyr Glu
            420                 425                 430

Trp Ala Ser Gly Phe Ser Met Arg Phe Gly Leu Leu Phe Val Asp Tyr
        435                 440                 445

Asn Thr Lys Arg Leu Tyr Trp Arg Pro Ser Ala Leu Val Tyr Arg Glu
    450                 455                 460

Ile Ala Thr Asn Cys Ala Ile Thr Asp Glu Ile Glu His Leu Asn Ser
465                 470                 475                 480

Val Pro Pro Val Lys Pro Leu Arg His
                485

<210> SEQ ID NO 9
<211> LENGTH: 285
<212> TYPE: PRT
<213> ORGANISM: Artificial Sequence
<220> FEATURE:
<223> OTHER INFORMATION: Consensus

<400> SEQUENCE: 9

Met Phe Pro Glu Phe Gly Gln Ser Gly Phe Gln Phe Glu Met Gly Pro
1               5                   10                  15

Asp Asp Trp Trp Trp Val Asp Asn Ile Gly Leu Val Ser Gly Asp Leu
            20                  25                  30

Pro Glu Gly Asn Trp Glu Leu Tyr Asp His Ala Lys Leu Gly Leu Asn
        35                  40                  45

Ala Tyr Arg Ile Glu Trp Ser Arg Ile Phe Pro Pro Thr Val Glu Ile
    50                  55                  60

Val Glu Leu Glu Leu Ala Asn Ala His Tyr Arg Ile Leu Lys Pro Gly
65                  70                  75                  80

Thr Ile Val Asn Leu His Thr Leu Pro Asp Trp His Asp Pro Ile Arg
                85                  90                  95

Gly Trp Leu Glu Arg Thr Val Glu Phe Ala Lys Tyr Ala Ala Tyr Val
            100                 105                 110

Ala Lys Phe Asp Asp Val Asp Trp Ser Thr Phe Asn Glu Pro Met Val
        115                 120                 125

Val Leu Gly Tyr Leu Tyr Ser Gly Phe Pro Pro Gly Leu Ser Pro Glu
    130                 135                 140

Ala Ala Lys Asn Ile Ala His Ala Ala Tyr Asp Ile Lys Ser Lys Pro
145                 150                 155                 160

Val Gly Ile Ile Tyr Asn Asp Pro Lys Asp Ala Ala Glu Phe Glu Ala
                165                 170                 175

Ile Gly Glu Pro Asp Trp Ile Gly Met Asn Tyr Tyr Thr Arg Val Val
            180                 185                 190

Glu Leu Pro Gly Tyr Gly Leu Ser Pro Ser Asp Phe Gly Trp Glu Tyr
        195                 200                 205
```

-continued

| | | | | | | | | | | | | | | |
|---|---|---|---|---|---|---|---|---|---|---|---|---|---|---|
| Arg | Glu | Gly | Leu | Tyr | Asp | Leu | Ala | Tyr | Pro | Tyr | Ile | Thr | Glu | Asn | Gly |
| | 210 | | | | 215 | | | | | 220 | | | | |
| Thr | Ala | Asp | Asp | Pro | Pro | Tyr | Ile | Ser | His | Val | Lys | Ala | Ile | Glu | Gly |
| 225 | | | | | 230 | | | | | 235 | | | | | 240 |
| Asp | Val | Pro | Gly | Tyr | Phe | His | Trp | Ser | Leu | Thr | Asp | Asn | Tyr | Glu | Trp |
| | | | | 245 | | | | | 250 | | | | | 255 | |
| Ala | Gly | Glu | Met | Arg | Glu | Gly | Leu | Glu | Val | Asp | Thr | Lys | Glu | Arg | Pro |
| | | | 260 | | | | | 265 | | | | | 270 | | |
| Arg | Ser | Ala | Val | Tyr | Arg | Glu | Ile | Ala | Ile | Glu | Leu | Arg | | | |
| | | 275 | | | | | 280 | | | | | 285 | | | |